(12) United States Patent
Yamazaki et al.

(10) Patent No.: US 7,238,857 B2
(45) Date of Patent: Jul. 3, 2007

(54) ETHYLENE-RESPONSIVE TRANSCRIPTION COACTIVATORS IN PLANTS

(75) Inventors: Ken-ichi Yamazaki, Sapporo (JP); Susumu Hirose, Mishima (JP)

(73) Assignee: Japan and Science and Technology Agency, Saitama (JP)

( * ) Notice: Subject to any disclaimer, the term of this patent is extended or adjusted under 35 U.S.C. 154(b) by 0 days.

(21) Appl. No.: 10/503,261

(22) PCT Filed: Feb. 6, 2003

(86) PCT No.: PCT/JP03/01207

§ 371 (c)(1), (2), (4) Date: Jul. 29, 2004

(87) PCT Pub. No.: WO03/068972

PCT Pub. Date: Aug. 21, 2003

(65) Prior Publication Data

US 2005/0132443 A1    Jun. 16, 2005

(30) Foreign Application Priority Data

Feb. 12, 2002    (JP)    ............... 2002-033512

(51) Int. Cl.
  *C12N 15/82*    (2006.01)
  *A01H 5/00*    (2006.01)
  *C07H 21/04*    (2006.01)

(52) U.S. Cl. ............ 800/283; 800/278; 800/298; 435/468; 435/419; 435/320.1; 536/23.6

(58) Field of Classification Search ............ 800/278, 800/283; 530/350, 370, 372; 536/23.1, 536/23.6; 435/320.1
See application file for complete search history.

(56) References Cited

U.S. PATENT DOCUMENTS

2005/0091708 A1 * 4/2005 Weglarz et al. ............ 800/278

OTHER PUBLICATIONS

Ozaki et al. Identificatin of the core domain and the secondary structure of the transcriptional coactivator MBF1 (1999) Genes to Cells, vol. 4, pp. 415-424.*
Branch AD. A good antisense molecule is hard to find. (1998) TIBS, vol. 23, pp. 45-50.*
Samac et al. Effect of chitinase antisense RNA expression on disease susceptibility of *Arabidopsis* plants. (1994) PMB, vol. 25, pp. 587-596.*
Nagata et al. Modification of tomato fruit ripening by transformation with sense or antisense chimeric 1-aminocyclopropane-1-carboxylate synthase genes. (1995) Acta Horticulturae, vol. 394, pp. 213-218.*
Chao et al. Activation of the ethylene gas response pathway in *arabidopsis* by the nuclear protein Ethylene-Insensitive3 and related proteins. (1997) Cell, vol. 89, pp. 1133-1144.*
GenBank Accession AP004663 (2002).*
Lewin B. Genes Third Edition (1987) Wiley and Sons, New York.*
Tieman et al. Members of the tomato LeEIL (EIN3-like) gene family are functionally redundant and regulate ethylene responses throughout plant development. (2001) The Plant Journal, vol. 26, pp. 47-58.*

* cited by examiner

*Primary Examiner*—Anne Kubelik
*Assistant Examiner*—Cathy Kingdon Worley
(74) *Attorney, Agent, or Firm*—Drinker Biddle & Reath LLP

(57) ABSTRACT

An ethylene-responsive transcription co-activator (MBF) acts on ethylene-responsive transcription factors (ERFs), which positively controls the expression of ethylene-responsive plant genes. A plant is transformed by the gene of the co-activator, and a promoter that may increase or decrease responsiveness to ethylene depending on its alignment. A method for controlling the responsiveness of plants to ethylene transforms a plant comprising an ERF-dependent gene, which positively control the expression of ethylene responsive genes of plants. This transcription co-activator gene is applied to control ethylene response of plants.

5 Claims, 6 Drawing Sheets

Fig. 1
ERE fragment
(wild type)
5'-gatctcaTAAGAGCCGCCactaaaataagaccgatcaaaTAAGAGCCGCCatg-3'
     3'-agtATTCTCGGCGGtgattttattctggctagtttATTCTCGGCGGtacctag-5'
mERE fragment
(mutant type)
5'-gatctcaTAAGATCCTCCactaaaataagaccgatcaaaTAAGATCCTCCatg-3'
     3'-agtATTCTAGGAGGtgattttattctggctagtttATTCTAGGAGGtacctag-5'
Fig. 2
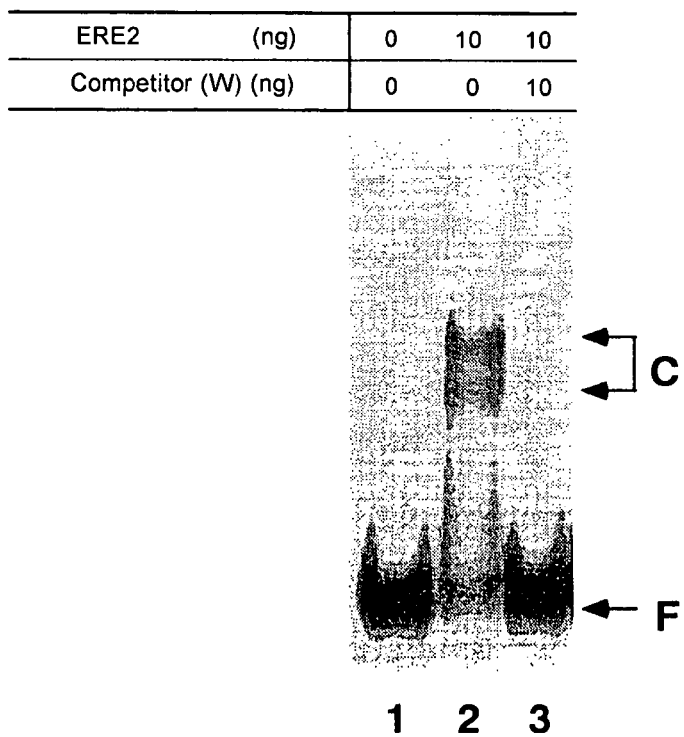
Fig. 3
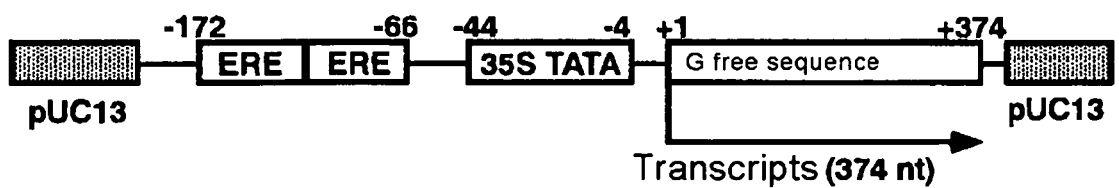

Fig. 6

```
  1  CAGAACCTTCTCTTCTTCCTTGTTCGTTCATCCCCTAACCCTTTCTTTGTTCATCTTGTT   60

61  CTTCCTCTTGTCGTCTCGTCGAGATGGCCGGGATTGGTCCGATCAGGCAGGACTGGGAGC  120
  1                          M  A  G  I  G  P  I  R  Q  D  W  E   12

121  CGGTGGTGGTGCGGAAGAAGGCGCCCACCGCCGCCGCCAAGAAGGATGAGAAGGCCGTCA  180
 13   P  V  V  V  R  K  K  A  P  T  A  A  A  K  K  D  E  K  A  V   32

181  ACGCCGCCCGCCGCTCCGGCGCCGAGATCGAGACCATGAAGAAGTATAACGCTGGAACAA  240
 33   N  A  A  R  R  S  G  A  E  I  E  T  M  K  K  Y  N  A  G  T   52

241  ACAAGGCGGCGTCCAGTGGCACATCCCTCAACACCAAGCGGCTGGATGACGACACCGAGA  300
 53   N  K  A  A  S  S  G  T  S  L  N  T  K  R  L  D  D  D  T  E   72

301  GCCTTGCCCATGAGCGTGTCTCAAGTGACCTGAAGAAAAACCTCATGCAAGCAAGGCTGG  360
 73   S  L  A  H  E  R  V  S  S  D  L  K  K  N  L  M  Q  A  R  L   92

361  ACAAGAAGATGACCCAGGCACAGCTTGCACAGATGATCAATGAGAAGCCCCAGGTGATCC  420
 93   D  K  K  M  T  Q  A  Q  L  A  Q  M  I  N  E  K  P  Q  V  I  112

421  AGGAGTACGAGTCAGGTAAAGCTATTCCGAACCAGCAGATCATCGGGAAGCTTGAAAGGG  480
113   Q  E  Y  E  S  G  K  A  I  P  N  Q  Q  I  I  G  K  L  E  R  132

481  CTCTTGGAACAAAGCTGCGCGGCAAGAAATAATGTTCTACTATTAGGCCCTGAAGCATAG  540
133   A  L  G  T  K  L  R  G  K  K                                142

541  TGTTGGAGCAACCAAAGCCAAAATGTTTGCGTAACCTATGCTGGGTCTTTTGATACCATG  600

601  CAGGATGTTTCTGTTGGTGCATGAGTGAATACTGAATAACTATTATGTTGTCGCAAACCT  660

661  TGTAATGCTGCCGCTCTTTGTGTGTCATAGTCCCTAGTGTGCAAGAGTTGTGCTGGACCT  720

721  TAAAACTGACTTGATAACCTGCGTGGTTTATGCATGATGTTTA<u>ATTAAAA</u>TATCAATGATC  780

781  TCTTTGGCTGTTTACAACTGAAAAAAAAAAAAAAAAAAAA                      819
```

Amount pf pERE-GUS transduced

Type and Dose(μ g) of Effector Plasmid Transduced

SEQUENCE LISTING

<160> NUMBER OF SEQ ID NOS: 6

<210> SEQ ID NO 1
<211> LENGTH: 142
<212> TYPE: PRT
<213> ORGANISM: Oryza sativa

<400> SEQUENCE: 1

```
Met Ala Gly Ile Gly Pro Ile Arg Gln Asp Trp Glu Pro Val Val Val
1               5                   10                  15

Arg Lys Lys Ala Pro Thr Ala Ala Lys Lys Asp Glu Lys Ala Val
            20                  25                  30

Asn Ala Ala Arg Arg Ser Gly Ala Glu Ile Glu Thr Met Lys Lys Tyr
        35                  40                  45

Asn Ala Gly Thr Asn Lys Ala Ala Ser Ser Gly Thr Ser Leu Asn Thr
    50                  55                  60

Lys Arg Leu Asp Asp Thr Glu Ser Leu Ala His Glu Arg Val Ser
65                  70                  75                  80

Ser Asp Leu Lys Lys Asn Leu Met Gln Ala Arg Leu Asp Lys Lys Met
                85                  90                  95

Thr Gln Ala Gln Leu Ala Gln Met Ile Asn Glu Lys Pro Gln Val Ile
            100                 105                 110

Gln Glu Tyr Glu Ser Gly Lys Ala Ile Pro Asn Gln Gln Ile Ile Gly
```

```
            115                 120                 125
Lys Leu Glu Arg Ala Leu Gly Thr Lys Leu Arg Gly Lys Lys
    130                 135                 140

<210> SEQ ID NO 2
<211> LENGTH: 819
<212> TYPE: DNA
<213> ORGANISM: Oryza sativa

<400> SEQUENCE: 2
cagaaccttc tcttcttcct tgttcgttca tccoctaacc ctttctttgt tcatcttgtt      60
cttcctcttg tcgtctcgtc gagatggccg ggattggtcc gatcaggcag gactgggagc     120
cggtggtggt gcggaagaag gcgcccaccg ccgccgccaa gaaggatgag aaggccgtca     180
acgccgcccg ccgctccggc gccgagatcg agaccatgaa gaagtataac gctggaacaa     240
acaaggcggc gtccagtggc acatccctca acaccaagcg gctggatgac gacaccgaga     300
gccttgccca tgagcgtgtc tcaagtgacc tgaagaaaaa cctcatgcaa gcaaggctgg     360
acaagaagat gacccaggca cagcttgcac agatgatcaa tgagaagccc caggtgatcc     420
aggagtacga gtcaggtaaa gctattccga accagcagat catcgggaag cttgaaaggg     480
ctcttggaac aaagctgcgc ggcaagaaat aatgttctac tattaggccc tgaagcatag     540
tgttggagca accaaagcca aaatgtttgc gtaacctatg ctgggtcttt tgataccatg     600
caggatgttt ctgttggtgc atgagtgaat actgaataac tattatgttg tcgcaaacct     660
tgtaatgctg ccgctctttg tgtgtcatag tccctagtgt gcaagagttg tgctggacct     720
taaaactgac ttgataacct gcgtggttta tgcatgatgt ttattaaaat atcaatgatc     780
tctttggctg tttacaactg aaaaaaaaaa aaaaaaaa                             819

<210> SEQ ID NO 3
<211> LENGTH: 53
<212> TYPE: DNA
<213> ORGANISM: Ipomoea tricolor

<400> SEQUENCE: 3
gatctcataa gagccgccac taaaataaga ccgatcaaat aagagccgcc atg             53

<210> SEQ ID NO 4
<211> LENGTH: 53
<212> TYPE: DNA
<213> ORGANISM: Ipomoea tricolor

<400> SEQUENCE: 4
gatccatggc ggctcttatt tgatcggtct tattttagtg gcggctctta tga             53

<210> SEQ ID NO 5
<211> LENGTH: 53
<212> TYPE: DNA
<213> ORGANISM: Ipomoea tricolor

<400> SEQUENCE: 5
gatctcataa gatcctccac taaaataaga ccgatcaaat aagatcctcc atg             53

<210> SEQ ID NO 6
<211> LENGTH: 53
```

-continued

```
<212> TYPE: DNA
<213> ORGANISM: Ipomoea tricolor

<400> SEQUENCE: 6
gatccatgga ggatcttatt tgatcggtct tattttagtg gaggatctta tga          53
```

ETHYLENE-RESPONSIVE TRANSCRIPTION COACTIVATORS IN PLANTS

BACKGROUND OF THE INVENTION

1. Field of the Invention

This invention relates to a transcription coactivator in ethylene-responsive transcription factors and further to a method for controlling ethylene-response of plants using the transcription coactivator.

2. Prior Art

Freshness of agricultural products such as crops and flowers is an essential factor to determine their commercial values. On the other hand, ethylene, a plant hormone, controls functions of plant cells during the processes from budding to senescence. Since ethylene, a plant hormone, has a profound effect on freshness, a lot of attention has been paid. The technique to control freshness by controlling ethylene has been a technique dreamed of by producers, distributors and retailers of agricultural products. If it is possible, there is a lot of economical usefulness in preventing overripe fruits and damaged flowers.

For example, a new variety of tomato, FLAVR SAVR®, wherein the expression of polygalacturonase of tomato is suppressed, is well known. Moreover, other trials to prevent overripe of tomato by repressing the expression of the gene of ethylene synthetic enzyme and the production of ethylene have been performed.

Previously, most of the trials in controlling ethylene response were by manipulating genes of transcriptional activation factors, which stimulate promoters of ethylene-responsive genes, or target genes of ethylene. These ethylene-responsive transcription factors (ERFs) have been known as regulatory factors positively controlling the expression of ethylene-responsive genes of plants (Ohme-Takagi, M. and Shinshi, H., (1995) Ethylene-inducible DNA binding proteins that interact with an ethylene-responsive element. Plant Cell 7: 173–182; Suzuki, K., Suzuki, N., Ohme-Takagi, M. and Shinshi, H., (1998) Immediate early induction of mRNAs for ethylene-responsive transcription factors in tobacco leaf strips after cutting. Plant J. 15: 657–665.)

For example, a report of November, 1996, entitled "Development of experimental systems for analysis of the mechanism of biophylaxis and the analysis of biophylaxis" announcing the results of a project on fundamental techniques to develop new experimental system for plants (the second term, 1993–1995), supported by Research and Development Bureau of Science and Technology Agency, tried to elucidate the molecular mechanism of biological control and response of plants by identifying functionally an ethylene-responsive cis-DNA element of biophylaxis gene, which is transcriptionally controlled by ethylene, by testing a reporter gene in transgenic plants and by identifying transcriptional regulatory gene interacting with said element.

Moreover, patent Disclosure 2000-50877 disclosed a method for providing resistance against environmental stresses for such plants as tobacco by introducing transcription factors controlling ethylene-inducible genes.

Still furthermore, U.S. Pat. No. 5,824,868 disclosed a method for lowering ethylene response of plants, wherein a plant is transduced with modified ethylene-responsive DNA, and a method for controlling the expression of said DNA.

PROBLEMS TO BE SOLVED BY THE INVENTION

The purpose of the present invention is to identify a transcription coactivator (transcriptional cofactor, MBF) in ethylene-responsive transcription factors (ERFs), to elucidate the mechanism of the action of MBF to ERFs, which positively control the expression of ethylene-responsive genes in plants, and further to provide a method for controlling the ethylene-response in plants.

MEANS OF SOLVING THE PROBLEMS

The gene to be used for controlling ethylene-response of this invention encodes Multiprotein Bridging Factor-1 (MBF-1), one of the transcriptional controlling factors necessary for ethylene-response.

A transcriptional controlling factor, in spite of the presence in only a few molecules per cell, is a very important factor for controlling an intracellular signal network. Changing slightly the amount of the expression of a gene of the factor could result in profound effect on various biological responses. Therefore, this invention provides a method for controlling freshness of a crop plant, by changing the expression amount of endogenous MBF-1 gene by transducing a gene to a plant, which leads to change the ethylene-response of the plant.

More specifically, the present invention is a protein of the following (a) or (b):

(a) A protein having an amino acid sequence shown by SEQ ID NO: 1.

(b) A protein having an amino acid sequence comprising a deletion, substitution or addition of one or several amino acids in the amino acid sequence of SEQ ID NO: 1, and having an enriched ethylene-response activity when expressed in plants.

Augmentation in ethylene response can be confirmed by an assay of the direct increase in ethylene-response of plants or an increase of expression of ERFs, e.g. the expression of ERF2 as hereinafter described.

Additionally, a gene encoding a polypeptide, whose function is similar to the polypeptide with the amino acid sequence (SEQ ID NO: 1) of MBF1 of *Oryza sativa*, which has been cloned by the inventors for the first time, could be found in other plants and the alignment of the amino acid sequence between the other plants and *Oryza sativa* shows the following sequence identity; AtMBF1a, 81.69%; AtMBF1b, 79.58%; AtMBF1c of *Arabidopsis thaliana*, 47.97%; StMBF1 of batata, 78.17%; RcMBF1 of caster-oil plant, 82.39%; LeMBF1 in tomato, 44.90%. The tomato gene, whose amino acid sequence identity to that of *Oryza sativa* is the lowest, is still induced by ethylene, therefore, these genes are suggested to be related to ethylene-responsive genes.

Furthermore, the present invention is a gene comprising the following DNA (a) or (b);

(a) A DNA having a nucleotide sequence shown by SEQ ID NO: 2.

(b) A DNA having a nucleotide sequence encoding said protein encoded by SEQ ID NO: 2.

Moreover, the present invention is a polynucleotide comprising a part of the gene. Still furthermore, the present invention is a polynucleotide comprising a promoter and the gene or polynucleotide, wherein said gene or polynucleotide is aligned in forward direction to said promoter. Still moreover, the present invention is a polynucleotide comprising a promoter and the gene or polynucleotide, wherein said gene or polynucleotide is aligned in reverse direction to said promoter.

The promoter as used herein includes the cauliflower mosaic virus 35S promoter, the heat shock promoter, chemical-inducible promoters and others.

Additionally, there are no limits on the way to link a promoter with said gene and the link can be operated appropriately using conventional techniques of genetic engineering.

Frequently, the expression of a target gene is repressed in a plant, wherein a part of the gene or cDNA of MBF1 gene or others is linked to a promoter in a reverse direction (referred to as "repression by antisense RNA"). Also, in the case that the gene is linked in forward direction and a large amount of mRNA is expressed, these mRNA are recognized as exogenous materials and are decomposed. As a result, the expression is repressed (referred to as "cosuppression technique" or "transwich technique"). These well known techniques in the art can be applied to the gene of this invention to repress the expression of said gene and therefore to inhibit ethylene-response of plants.

Still moreover, this invention is a plasmid comprising said polynucleotide. The plasmids as used therein comprise binary vectors such as Ti plasmid and pBI-121 plasmid.

Still furthermore, this invention is a plant, wherein the plant is transformed by said polynucleotide. This invention is applicable to such monocotyledons as *Oryza sativa*, *zea mays*, wheat, et al. or to such dicotyledons as tomato et al.

These plants can be transformed using a conventional technique of genetic engineering, i.e. the gene of this invention can be inserted into said plasmid and the plasmid is used to transform said plants.

BRIEF DESCRIPTION OF DRAWINGS

FIG. 1 shows the nucleotide sequence of the DNA probe used in reference example 1. Both the wild-type ERE (the above chart; SEQ ID NO: 3) and the mutant-type ERE (mERE, the lower chart; SEQ ID NO: 5) are shown in the FIG. 1. Each DNA probe includes 2 copies of GCC box (bold face) or mutant-type GCC box.

FIG. 2 shows electrophoretic gel shift assays showing specific binding of ERF2 to ERE. F denotes a free DNA probe without binding and C denotes a DNA-ERF2 binding complex.

FIG. 3 shows the structure of plasmid DNA template (pERE) used in in vitro transcription.

FIG. 6 shows the nucleotide sequence (SEQ ID NO: 2) of cDNA of MBF 1 of *Oryza sativa* (oMBF1) and the amino acid sequence (SEQ ID NO: 1, corresponding to the position 85–510 of SEQ ID NO: 2) expected from the nucleotide sequence. The underlined sequence denotes the poly A addition signal.

DESCRIPTION OF PREFERRED EMBODIMENTS

Figure 4:
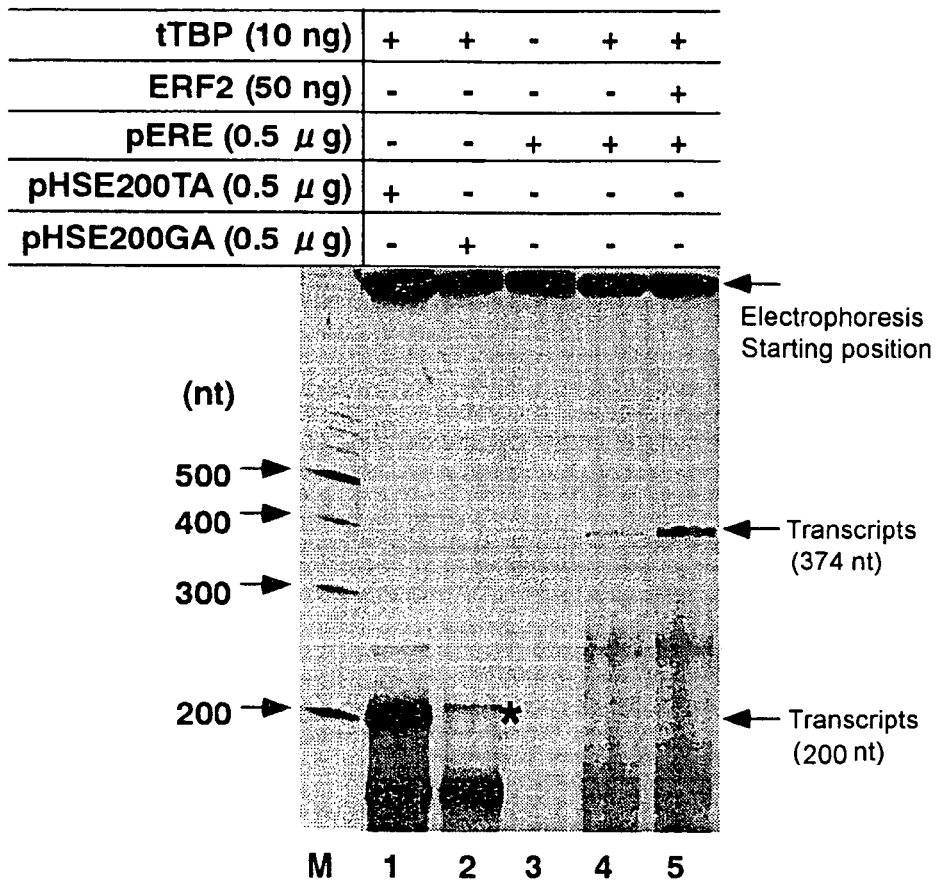
FIG. 4 shows the electrophoresis of transcripts using different DNA templates; pHSE200TA (lane 1); pHSE200GA (lane 2); pERE (lanes 3–5). Under the condition of presence or absence of purified recombinant proteins as shown above each lane, RNA was synthesized using each plasmid DNA template. In the figure, M denotes a marker for molecular weight of single strand DNA and * denotes transcripts independent of TATA box.

In the present invention, the inventors succeeded in specifying a transcription coactivator (SEQ ID NO: 1 and 2) in a family of ethylene-responsive transcription factors. Furthermore, the inventors confirmed that the transcription coactivator was for ERF, positively controlling the expression of a set of ethylene-responsive plant genes.

It is possible to use the transcription coactivator gene of this invention to control the ethylene response of plants. Previously, to control the ethylene response of plants, people tried to change a target gene of ethylene response or tried to change a gene producing ethylene. However, changing the gene encoding a transcription coactivator as an informational molecule as described in this invention makes it possible to control the expression of the target genes in toto and hence has greater influence than previous methods.

The following examples illustrate this invention, however, it is not intended to limit the scope of the invention.

EXAMPLES

Reference Example 1

The specific binding of purified recombinant ethylene-responsive transcription factors (ERFs) to ethylene responsive element (ERE) was examined in this example.

To examine specific binding of ERFs to ERE, the inventors induced overexpression of tobacco-derived ERF in *E. coli* and purified it. Inserting DNA region encoding ERF protein from each of four kinds of tobacco into expression plasmid pET 15b (Novagen, Madison, Wis.), the inventors induced high levels of expression of recombinant ERF proteins in *E. coli* (BL21/DE3/pLysS). The four kinds of recombinant proteins were purified using Ni immobilized resins (His•Bind® resin, Novagen; an uncharged IDA agarose resin). The tobacco-derived recombinant TBP (tTBP) was purified by the method reported previously (Biosci. Biotech. Biochem., 58:916–920 (1994)). The purity and size of the purified recombinant proteins were examined by ordinal SDS-PAGE (15% separation gel; Nature 227:680–685b (1970). Confirming the molecular weight of each ERF protein by SDS-PAGE, the inventors found that the size was slightly larger than the size calculated based on the amino acid sequence expected from cDNA nucleotide sequence (30–45 kDa).

The binding activity of ERF2 to ERE was investigated using gel-shift assays. The DNA fragment containing a 53 bp wild-type ethylene-responsive element (ERE) was used as a DNA probe after labeled with a radioactive tracer using $(\gamma^{-32P})$ATP and T4-polynucleotide kinase (Takara Bio INC., Kyoto, Japan). Multi-copied and linked ERE (SEQ ID NO: 3 and 4) or mERE (SEQ ID NO: 5 and 6) fragments (FIG. 1) were used as wild-type and mutant-type competitors, respectively. mERE (mutant-type) was similar to ERE (wild-type), except that the DNA nucleotide sequence in the GCC box contains base substitutions. The mixture of 1 ng of radio-labeled DNA probe (1,000 to 10,000 cpm) and 10 ng of recombinant ERF without or with 10 ng of a competitor DNA in 10 µl of the binding buffer shown in Table 1 was incubated for 45 minutes at 25° C.

TABLE 1

| | |
|---|---|
| 25 mM | Hepes-KOH (pH 8.0) |
| 40 mM | KCl |
| 0.1 mM | EDTA |
| 1 mM | DTT |
| 20% | glycerol |
| 250 ng | poly(dA-dT)::(dA-dT) |
| 0.1% | tritonX-100 |

The samples after binding reaction were subjected to 4% polyacrylamide gel electrophoresis (acrylamide:bisacrylamide=39:1, 1 mm in thickness, 13 cm long) containing 0.25×TB buffer (22.5 mM Tris-borate, pH 8.0) at 25° C. for 3 hrs at 100 V. The gel was dried and exposed to Fuji Imaging Plate® (Fuji Photo Film Co. Ltd., Kanagawa, JAPAN; a radiosensitive layer of phosphor crystals on a polyester backing plate). The electrophoresis mobility pattern was visualized using Bio-Image Analyzer (Fuji Photo Film Co. Ltd., Kanagawa, JAPAN). The results are shown in FIG. 2. In the figure, F denotes free DNA probe without binding and C denotes DNA-ERF2 binding complex.

Reaction of 10 ng of ERF2 with 1 ng of radio-labeled DNA probe resulted in a shift of the DNA band to a larger size, which demonstrates the formation of a DNA and protein complex (FIG. 2).

Since the formation of the DNA-protein complex was inhibited by the addition of cold ERE fragments but not by the addition of cold mERE, the complex formation depends on a specific binding. Furthermore, three other kinds of transcription factors, i.e. ERF1, ERF3 and ERF4, similarly bind to ERE.

Reference Example 2

In this example, the inventors showed that ERE-dependent transcription was amplified by ERF2 in HeLa nuclear extracts (HNE).

The plasmid DNA used for the in vitro transcription was constructed in the following way. To construct plasmid DNA template (pERE) as shown in FIG. 3, two copies of ERE DNA fragments (FIG. 1) were inserted to Bgl II site of the plasmid pU35 as reported previously (Pro. Natl. Acad. Sci. USA 87:7035–7039(1990)). As in the case of pmERE plasmid DNA template, two copies of mERE were inserted in said way instead of ERE. The construction of control plasmid DNA template, pHSE200TE and pHSE200GA, is as already reported (Plant Mol. Biol. 34:69–79(1997)).

Moreover, the in vitro transcription reaction was assayed in the following way. The HeLa nuclear extracts used for the in vitro transcription were prepared as reported previously (Meth. Enzymol. 101:582–598(1983)). The composition of the standard in vitro transcription reaction mixture is shown in Table 2.

TABLE 2

| 1. Reaction mixture of in vitro transcription | |
|---|---|
| 18.4 mM | Hepes-KOH pH 7.9 |
| 51.2 mM | KCl |
| 4.5 mM | Mg(CH$_3$COO)$_2$ |
| 0.08 mM | EDTA |
| 1.12 mM | DTT |
| 16% (w/v) | glycerol |
| 0.048% | TritonX-100 |
| 0.1 mM | ATP |
| 0.1 mM | CTP |
| 0.01 mM | UTP |
| 5 µCi | [$\alpha^{-32P}$]UTP specific activity 400–800 Ci/m mol) |
| 0.5 µg | plasmid DNA template |
| 0.04 mM | 3'-0-methyl-GTP |
| 20 units | RNase T1 |
| 10 µg | protein HeLa nuclear extracts (HNE) |
| 2. Reaction stopping solution | |
| 5% | SDS |
| 10 mM | EDTA |
| 0.4 mg/ml | glycogen |
| 150 mM | sodium acetate |

The transcription reaction mixture was incubated for 60 min at 30° C. and 75 µl of the reaction stopping solution (Table 2) was added to stop the reaction. Then, 100 µl of PCIAA (50% phenol, 48% chloroform, 2% isoamilalcohol) was added to the reaction mixture to recover the aqueous phase. After that, 100 µl of CIAA (96% chloroform, 4% isoamilalcohol) was added to the aqueous phase and the aqueous phase was recovered. Then, 10 µl of 3 M sodium acetate and 300 µl of ethyl alcohol were added to the aqueous phase to precipitate nucleic acid. The nucleic acid was dried and was dissolved in 10 µl of urea solution (5M urea, 1 mM EDTA, 0.1% bromophenol blue). The nucleic acid sample was subjected to electrophoresis using 6% polyacrylamide gel (acrylamide:bisacrylamide=19:1, 1 mm of thickness, 12.5 cm long) containing 89 mM Tris-borate (pH 8.3), 2 mM EDTA and 8 M urea at 300 V. When bromophenol blue in the sample had migrated to the lowest edge of the gel, the gel was removed and was soaked in 1 L of water containing 5% methanol and 5% acetic acid and then in 1 L of water containing 5% methanol, each for 20 min. Then, the gel was attached to a filter paper, dried and exposed to Fuji Imaging Plate overnight. RNA was visualized using Bio Image Analyzer.

To confirm TATA box-dependent initiation of transcription on plasmid DNA template in HNE (HeLa nuclear extracts), the inventors used pHSE200TA and PHSA200GA (Plant Mol. Biol., 34:69–79(1997)) as control plasmid DNA templates in the presence of recombinant tobacco TBP (tTBP). pHSE200TA contains 200 bp sequences of promoter region in the gene encoding heat shock proteins of *Arabidopsis* plants and 200 bp transcriptional region not containing guanine residue in the sense strand. pHSA200GA has a similar structure as pHSE200TA except that all T residues in TATA box (TATAAAT) in pHSE200TA are substituted to G (GAGAAAG).

FIG. 4 shows the results of electrophoresis of the transcripts using these DNA templates. When pHSE200TA was used as a DNA template, 200 nt of transcripts synthesized specifically was observed (lane 1). While, pHSE200GA provided a faint signal ascribed to TATA box-independent transcripts (lane 2).

The biochemical function of purified recombinant ERF2 as a transcriptional activating factor was assayed using pERE (FIG. 3) as a transcriptional template. Since no specific transcripts were observed using pERE as a transcriptional template without adding ERF2 (lane 3), tTBP of tobacco was added to increase basic transcriptional activity and a 374 nt signal corresponding to a specific transcript was observed (lane 4). Then, the addition of ERF2 and tTBP, amplified the signal observed in lane 4 (lane 5). In contrast, no amplification of transcripts was observed using pmERE (a plasmid substituted 2 copies of cis element (ERE) in pERE with 2 copies of mERE) as a transcriptional template (data not shown).

These observations demonstrate that recombinant ERF2 binds to ERE in HeLa nuclear extracts and functions as a transcriptional activator.

Reference Example 3

Figure 5:
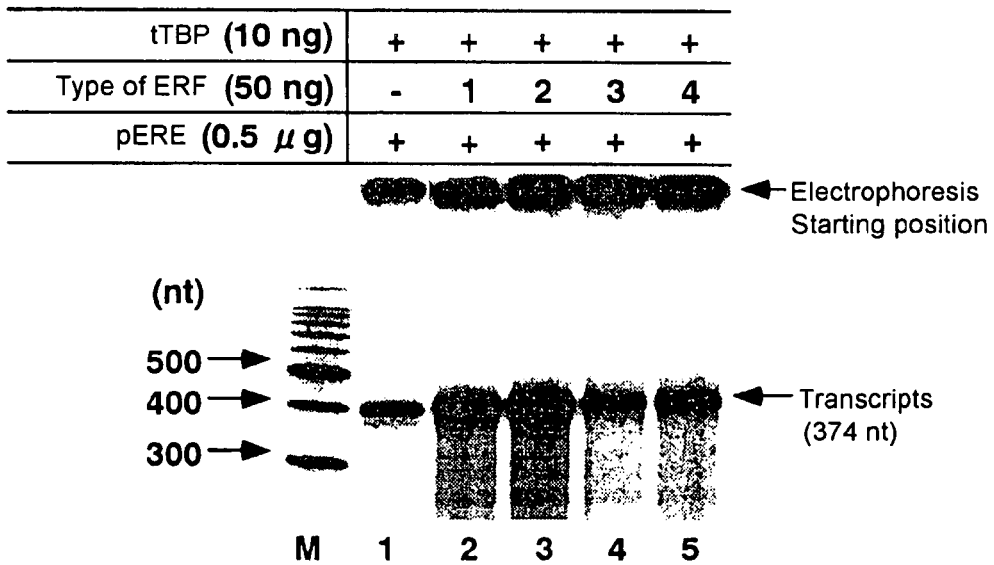
FIG. 5 shows the electrophoresis of transcripts using the plasmid DNA template (pERE) in the presence of various purified recombinant proteins as shown above each lane.
Figure 7:
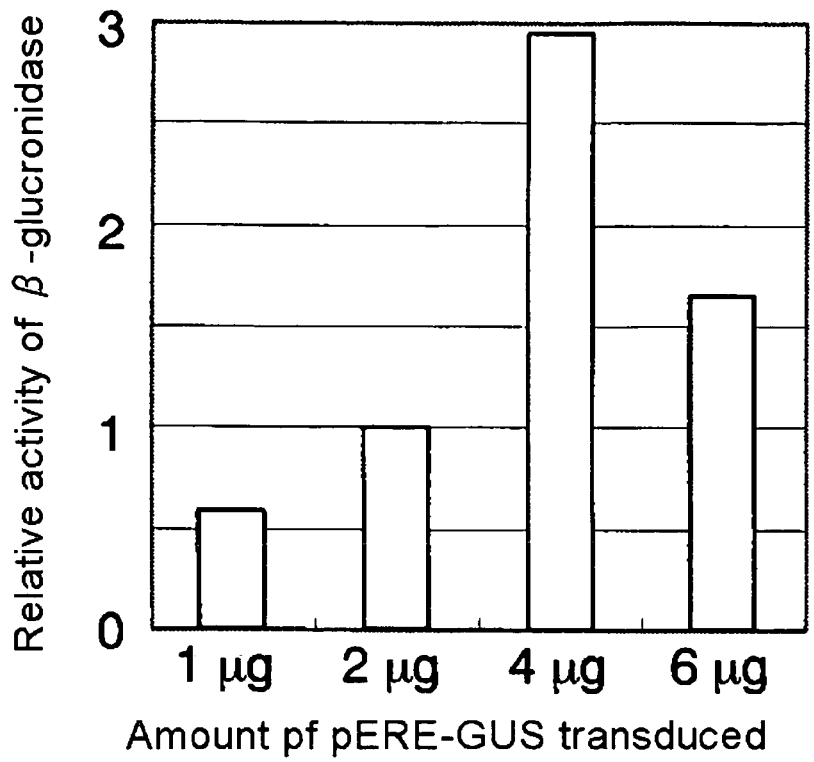
FIG. 7 shows the effect of reporter plasmid DNA (pERE-GUS) on the transcription in transient transcription assays using tobacco leaves. The ordinate denotes the increase of GUS activity dependent on the amount of reporter plasmid DNA (pERE-GUS) introduced to tobacco leaves. The values in the figure are averages of two independent experiments.

As in the case of reference example 2, the inventors examined the activity of transcriptional activation of other ERFs. As shown in FIG. 5, the addition of each of 4 kinds of ERF, i.e. ERF1 to ERF4, to the standard in vitro transcription assay system resulted in 3 to 5 fold increase in the transcription initiation rate on pERE. On the other hand, since these ERFs produced no observed effects on transcription initiation using pmERE as a template, each ERF was demonstrated to function as a transcriptional activator dependent on ERE in HeLa nuclear extracts. The activity of transcriptional activation of each ERF was as follows; amplification by ERF3, 3 fold; that by ERF4, 3.5 fold; that by ERF1, 4 fold; that by ERF2, 5 fold.

Example 1

In this example, the inventors showed that the gene expression dependent on an ethylene-responsive promoter was amplified by oMBF1 in the presence of ERF2. To check the possibility of involvement of multi protein bridging factor 1 (MBF1) in transcriptional amplification dependent on ethylene-responsive promoter, the inventors selected a candidate gene encoding MBF1 of *Oryza sativa* from the EST library of *Oryza sativa* prepared by the Ministry of Agriculture, Forestry and Fisheries of Japan. FIG. 6 shows the cDNA nucleotide sequence (SEQ ID NO: 2) encoding MBF1 of *Oryza sativa* (oMBF1) and the expected amino acid sequence (SEQ ID NO: 1, corresponding to position 85 to 510 of SEQ ID NO: 2). This amino acid sequence (SEQ ID NO: 1) is 81% homologous to the sequence of *Arabidopsis* MBF1 (AtMBF1) and is considerably higher than the homology (53%) to human MBF1 (hMBF1).

To show the function of MBF1 as a transcription coactivator, the inventors constructed an effector plasmid DNA (p35S-MBF1) which expresses MBF1 in tobacco cells, in the following way. To construct p35S-ERF2 and p35S-MBF1 effector plasmid DNA, the inventors deleted XbaI-Sac I fragment of plasmid vector pBI221 (CLONTECH Laboratories Inc., CA), which is the β-glucronidase coding region, and inserted the cDNA fragment (SEQ ID NO: 2) containing the cDNA of tobacco ERF2 (accession No. ABO 16264) and the cDNA of *Oryza sativa* MBF1 (SEQ ID NO: 2), which include an Xba I site and a Sac I site, added to the upstream and the downstream region, respectively, by PCR. The structures of pERE-GUS and pmERE-GUS, reporter plasmid DNA, correspond to 2(GCC)Gus and 2(mGCC) Gus, respectively, as used in the previous report (Plant Cell 7: 173–182 (1995)).

p35S-LUC, used as a control plasmid, was constructed by the replacement of the Xba I-Sac I fragment of said pBI221 by the Xba I-Sac I fragment sandwiching cDNA (accession No. E08319) of fire fly luciferase.

Plasmid DNA used in this example are summarized in Table 3.

TABLE 3

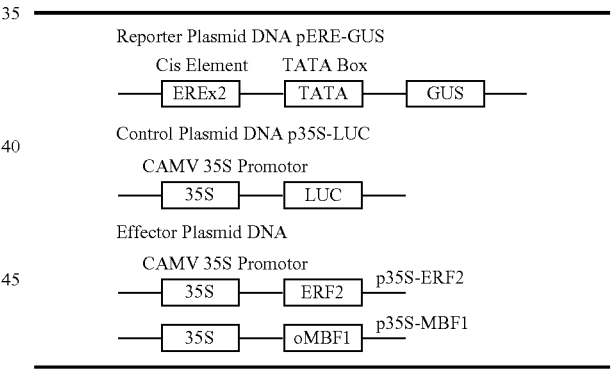

In the table, GUS denotes *E. coli*-derived β-glucronidase gene (β-D-glucronidase) and LUC denotes luciferase gene derived from fire fly or *Vibrio* oceanic luminiferous bacteria.

p35S-MBF1 was introduced into tobacco leaves by the microprojectile bombardment method (gold particles were coated with DNA and were introduced into intact plants by Helium pressure-driven particle inflow gun) and induced transient expression of oMBF1 for functional evaluation. The method of the evaluation was as follows. The transient assays using tobacco leaves were according to the previous report (Plant Mol, Biol. Reporter 18:101–107 (2000)). 2 μg of reporter plasmid DNA (pERE-GUS), 1 μg of control plasmid DNA (p35S-LUC) and various amounts of effector plasmid DNA were mixed with 0.5 mg of gold particles (1.5–3.0 μm in diameter, Aldrich Chem. WI) in 30 μl of TE buffer. Then, 3 μl of 3 M sodium acetate and 100 μl of ethanol was added to the mixture and the mixture was centrifuged. The gold particles coated with DNA were recovered and suspended in 100 μl of ethanol. Then, the suspension was dispersed by ultrasound and 5 μl of the dispersion was introduced to tobacco leaves, which had been cultured for 2 weeks, using Helium pressure-driven IDERA GIE-III (TANAKA Co. Ltd., Sapporo, Japan). After transduction of genes, tobacco leaves kept under light for 12 hrs at 25° C., were frozen in liquid nitrogen and were powdered using MIKRO-DISMEMBRATOR II (B. Brown Biotech International, Germany). Samples were divided in two and one portion was used to assay β-glucronidase activity using GUS-light chemiluminescence kit (TROPIX, MA). The other potion was used to assay luciferase activity using a luciferase reporter assay system (Promega Corp., WI) and Luminescencer-JNR luminometer (ATTO Co, Ltd., Tokyo, Japan).

β-glucronidase activity, which is an indicator of gene expression dependent on an ethylene-responsive promoter, was corrected based on this luciferase activity. First of all, various doses of reporter plasmid DNA (pERE-GUS) were coated on the surface of gold particles and were introduced into tobacco leaves. Then, dynamic ranges of β-glucronidase activity were assayed. The results are shown in FIGS. 7–10. In these experiments, 1 μg of control plasmid DNA (p35S-LUC) is always mixed in each sample as an internal control; then by assaying luciferase activity of each sample, a yield of gene transduction was calculated and β-glucronidase activity of each experiment was corrected.

Figure 8:
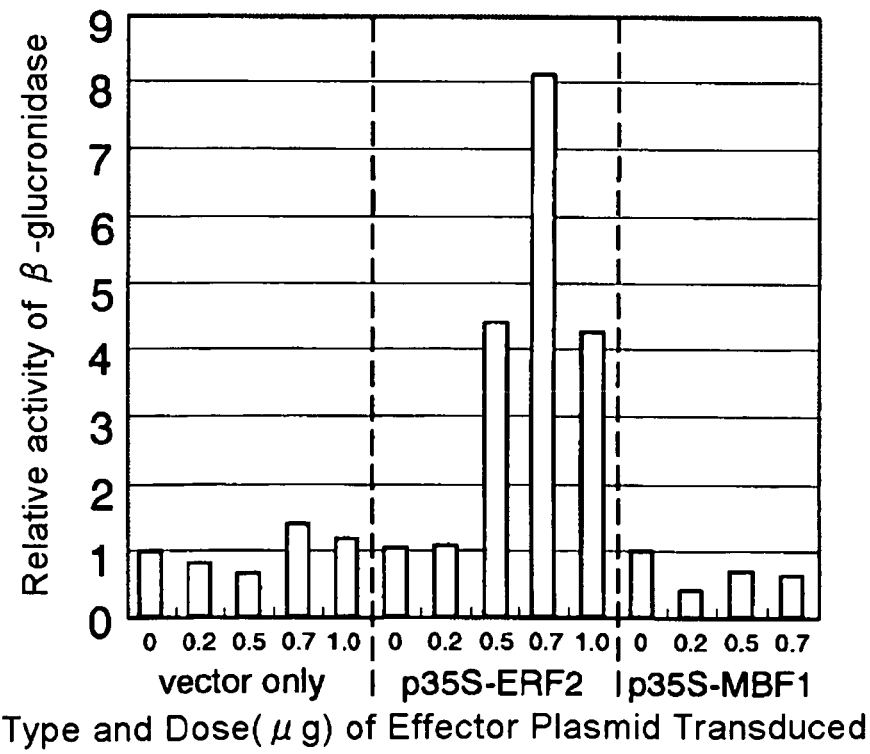
FIG. 8 shows the effect of the addition of a transcription factor (ERF2) or a transcription coactivator (oMBF1) on transient assays using tobacco leaves. The figure shows the effect of changing amount of ERF2 and oMBF1 on the amount of transcripts using a reporter plasmid DNA. Under each bar chart, there are shown the type and the amount of effector plasmid DNA used. The values in the figure are averages of the results of two independent experiments.

As a result, β-glucronidase activity increased linearly as the dose of pERE-GUS increased from 1 μg to 4 μg, then the activity slightly decreased as the dose of pERE-GUS increased to 6 μg. Therefore, in the following transient assays 2 μg of pERE-GUS and 1 μg of p35S-LUC were added to all the DNA mixtures. The addition of 0.2 μg of the effector plasmid DNA (p35S-ERF2) to said mixture does not demonstrate an increase of GUS activity, but further addition of the effector plasmid DNA (up to 0.7 μg) increased GUS activity (FIG. 8 center). Furthermore, the addition of only different amount of p35S-MBF1 as an effector plasmid DNA led to no change in GUS activity (FIG. 8 right).

Figure 9:
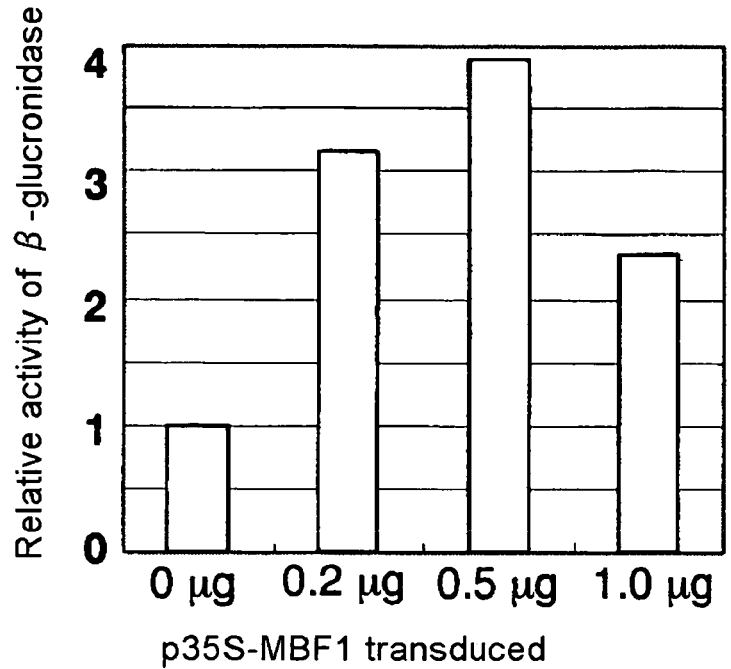
FIG. 9 shows the amplified activity of the transcriptional activator, ERF2, by oMBF1 in transient assays using tobacco leaves. The figure shows the effect of the concentration of oMBF1 on the transcription of a reporter plasmid DNA under the control of ERF2. As shown under each bar chart, each reaction mixture was added various amount of p35S-MBF1 in addition to 2 μg of pERE-GUS, 1 μg of p35S-LUS and 0.2 μg of p35S-ERF2. The values in the figure are averages of the results of two independent experiments.
Figure 10:
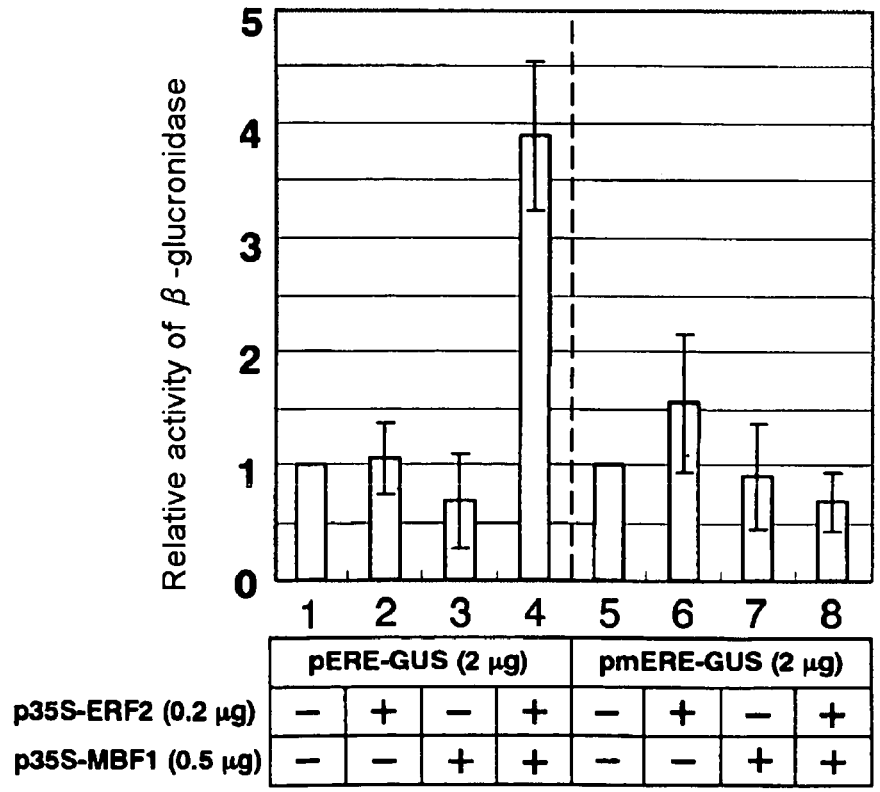
FIG. 10 shows the amplified activity of the transcriptional activator, ERF2, by oMBF1 in transient assays using tobacco leaves. The figure shows the amplified transcription dependent on the nucleotide sequence of ERE under the control of ERF2 and oMBF1. The reporter and effector plasmid DNA shown under each bar column are mixed and transduced to tobacco leaves. The values in the figure are averages of the results of three independent experiments.

On the other hand, in the presence of 0.2 μg of the first effector plasmid DNA (p35S-ERF2), the addition of different amounts of the second effector plasmid DNA (p35S-MBF1) increased GUS activity in a dose dependent manner (FIG. 9). Additionally, in the presence of both ERF2 and MBF1, GUS activity increased cooperatively (FIG. 10 left). The cooperative increase of GUS activity in the presence of ERF2 and MBF 1 was observed only when pERE-GUS was used as reporter plasmid DNA, but not when pmERE-GUS was used (FIG. 10 right).

These observations demonstrate that oMBF1 is a transcription coactivator for ERF2.

Example 2

To examine whether oMBF1 functions as a transcription coactivator for clones other than ERF2, e.g. ERF4, the inventors carried out an experiment similar to example 1 by replacing p35S-ERF2 by p35S-ERF4. The results are shown in FIGS. 11 and 12.

Figure 11:
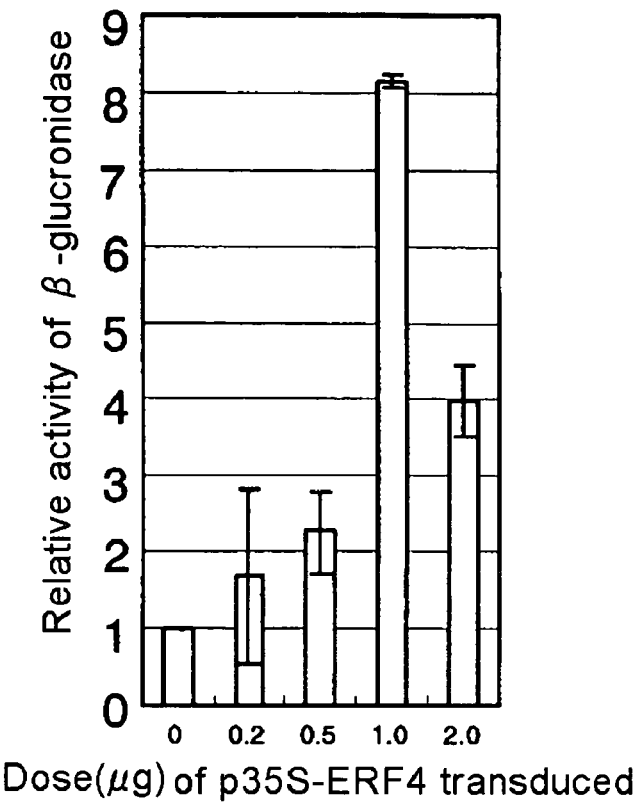
FIG. 11 shows the amplified activity of the transcriptional activator, ERF4, by oMBF1 in transient assays using tobacco leaves. The effect of the amount of ERF4 on the transcripts of a reporter plasmid DNA is shown in the figure. In each experiment, 2 μg of pERE-GUS is used as the reporter plasmid DNA. Under each bar column, the types and the amount of effector plasmid are shown. The values in the figure are averages of three independent experiments.
Figure 12:
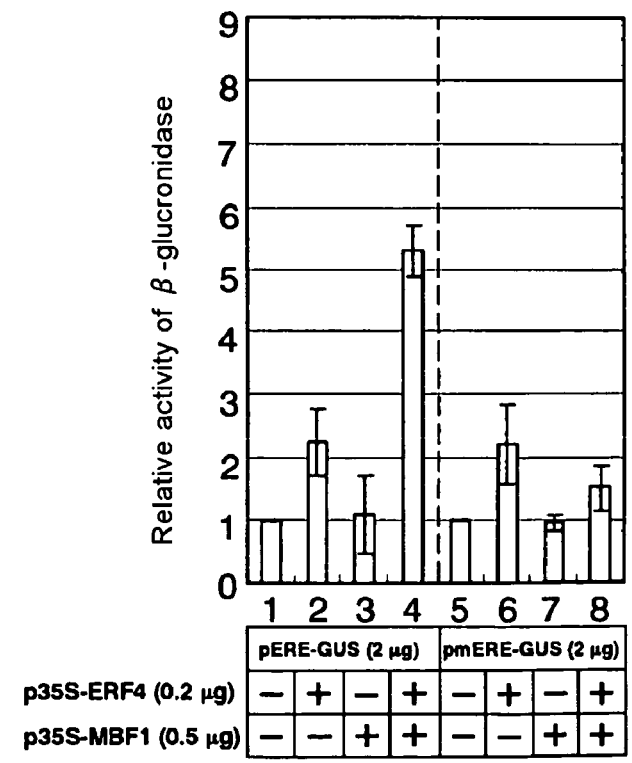
FIG. 12 shows the amplified activity of the transcriptional activator, ERF4, by oMBF1 in transient assays using tobacco leaves. The ERF4 and oMBF1-dependent amplification of transcripts dependent on ERE nucleotide sequence is shown in the figure. The reporter and effector plasmid DNA shown on the bar column are mixed and are transduced to tobacco leaves. The values in the figure are averages of three independent experiments.

Several fold change in GUS activity in a dose dependent manner was observed with the addition of 0.5 μg to 1.0 μg of p35S-ERF4, however, only 1.7 fold change was observed at 0.2 μg of p35S-ERF4 (FIG. 11). Furthermore, 5.5 fold increase of GUS activity was observed by further addition of 0.5 μg of p35S-MBF1 in the presence of 0.2 μg of p35S-ERF4 (FIG. 12 left), while no increase in GUS activity was observed by the replacement of the reporter plasmid DNA by pmERE-GUS (FIG. 12 right).

These observations demonstrate that oMBF1 functions as a transcription coactivator for ERF4 as well as ERF2.

The invention claimed is:

1. An isolated polynucleotide comprising the polynucleic acid of SEQ ID NO: 2.

2. A construct comprising a plant promoter and the polynucleic acid of SEQ ID NO: 2, wherein the polynucleic acid is operably linked to the plant promoter.

3. A vector comprising the construct of claim 2.

4. A plant that is transformed with the construct of claim 2.

5. A method for increasing a plant's responsiveness to ethylene, comprising transforming a plant with the construct of claim 2.

* * * * *